US012622889B2

(12) United States Patent
Millet et al.

(10) Patent No.: US 12,622,889 B2
(45) **Date of Patent: *May 12, 2026**

(54) S-β-HYDROXYBUTYRATE ESTERS FOR IMPROVING METABOLIC FUNCTION

(71) Applicant: AXCESS GLOBAL SCIENCES, LLC, Washington, UT (US)

(72) Inventors: Gary Millet, Washington, UT (US); Ryan Lowery, Tampa, FL (US); Jacob Wilson, Tampa, FL (US); Terry Lacore, Melissa, TX (US)

(73) Assignee: AXCESS GLOBAL SCIENCES, LLC, Washington, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/315,079

(22) Filed: Aug. 29, 2025

(65) Prior Publication Data

US 2025/0381162 A1 Dec. 18, 2025

Related U.S. Application Data

(60) Continuation-in-part of application No. 19/221,260, filed on May 28, 2025, and a continuation-in-part of application No. 19/096,389, filed on Mar. 31, 2025, which is a continuation of application No. 18/977,541, filed on Dec. 11, 2024, now Pat. No. 12,350,243, which is a continuation of application No. 18/592,262, filed on Feb. 29, 2024, now Pat. No. 12,329,734, which is a continuation of application No. 18/219,556, filed on Jul. 7, 2023, now Pat. No. 12,251,362, which is a continuation-in-part of application No. 18/218,519, filed on Jul. 5, 2023, now Pat. No. 11,944,598, which is a continuation-in-part of application No. 17/555,724, filed on Dec. 20, 2021, now Pat. No. 11,786,499, which is a continuation of application No. 17/367,206, filed on Jul. 2, 2021, now Pat. No. 12,109,182, which is a continuation of application No. 17/130,498, filed on Dec. 22, 2020, now Pat. No. 11,202,769, which is a continuation-in-part of application No. 16/783,886, filed on Feb. 6, 2020, now Pat. No. 11,185,518, which is a continuation-in-part of application No. 16/272,192, filed on Feb. 11, 2019, now Pat. No. 10,596,130, which is a continuation-in-part of application No. 16/224,485, filed on Dec. 18, 2018, (Continued)

(51) Int. Cl.

| | |
|---|---|
| ***A61K 31/22*** | (2006.01) |
| ***A61K 9/00*** | (2006.01) |
| ***A61K 31/047*** | (2006.01) |
| ***A61K 31/19*** | (2006.01) |

(52) U.S. Cl.
CPC ............ *A61K 31/22* (2013.01); *A61K 9/0053* (2013.01); *A61K 31/047* (2013.01); *A61K 31/19* (2013.01); *A23V 2200/3322* (2013.01)

(58) Field of Classification Search
CPC .... A61K 31/22; A61K 9/0053; A61K 31/047; A61K 31/19; A23V 2200/3322
See application file for complete search history.

(56) References Cited

U.S. PATENT DOCUMENTS 2,238,149 A 4/1941 Aeckerle
2,976,073 A 3/1961 Russell et al.

(Continued)

FOREIGN PATENT DOCUMENTS

CA 2990927 A1 7/2018
CN 86108978 A 11/1987

(Continued)

OTHER PUBLICATIONS

Veech, "The Therapeutic Implications of Ketone Bodies: The Effects of Ketone Bodies in Pathological Conditions: Ketosis, Ketogenic Diet, Redox States, Insulin Resistance, and Mitochondrial Metabolism", Prostaglandins Leukot Essent Fatty Acids, Mar. 2004, 70(3), pp. 309-319.
Veech, et al., "Ketone Bodies Mimic the Life Span Extending Properties of Caloric Restriction", IUBMB Life Feb. 8, 2017.
Vorgerd, M. and J. Zange. Treatment of glycogenosys type V (McArdle disease) with creatine and ketogenic diet with clinical scores and with 31P-MRS on working leg muscle. Acta Myologica, 2007; XXVI; pp. 61-63.
Walton, G. et al. A randomised, double-blind, placebo controlled cross-over study to determine the gastrointestinal effects of consumption of arabinoxylan-oligosaccharides enriched bread in healthy volunteers, 2012, Nutrition Journal, 11(36): 1-11 (Year: 2012).

(Continued)

*Primary Examiner* — Deborah D Carr
(74) *Attorney, Agent, or Firm* — Workman Nydegger

(57) ABSTRACT

Compositions for improving metabolic function in a subject include optically pure S-beta-hydroxybutyrate or non-racemic mixtures enriched with the S-enantiomer. S-beta-hydroxybutyrate in pure or enriched form provides energy to the heart, dilates the arteries, decreases blood pressure and systemic vascular resistance, and increases cardiac output. S-Beta-hydroxybutyric acid is more rapidly absorbed and utilized by the body than salts or esters, enhances taste, and reduces the need to include citric acid or other edible acids. S-Beta-hydroxybutyrate salts are more slowly absorbed and utilized by the body and provide one or more electrolytes. S-Beta-hydroxybutyrate esters provide more controlled release without adding electrolytes. Compositions for improving heart function in a subject may contain a dietetically or pharmaceutically acceptable carrier and optically pure S-beta-hydroxybutyrate or non-racemic mixture enriched with S-beta-hydroxybutyrate, wherein the compositions contain from about 50.5% to 100% by enantiomeric equivalents of S-beta-hydroxybutyrate and from about 49.5% to 0% by enantiomeric equivalents of R-beta-hydroxybutyrate.

20 Claims, No Drawings

Related U.S. Application Data now Pat. No. 10,596,128, which is a division of application No. 15/936,849, filed on Mar. 27, 2018, now Pat. No. 10,245,243, which is a continuation-in-part of application No. 15/491,924, filed on Apr. 19, 2017, now Pat. No. 11,173,138.

(60) Provisional application No. 62/607,578, filed on Dec. 19, 2017, provisional application No. 62/324,798, filed on Apr. 19, 2016.

(56) References Cited

U.S. PATENT DOCUMENTS 4,139,761 A 2/1979 Obrowski
4,224,503 A 9/1980 Gijzel et al.
4,292,499 A 9/1981 Kleinschmidt et al.
4,627,808 A 12/1986 Hughes
4,771,074 A 9/1988 Lammerant et al.
4,969,393 A 11/1990 Mahlich et al.
4,997,976 A 3/1991 Brunengraber et al.
5,093,044 A 3/1992 Wretlind et al.
5,100,677 A 3/1992 Veech
5,116,868 A 5/1992 Chen et al.
5,288,512 A 2/1994 Seiden
5,292,774 A 3/1994 Hiraide et al.
5,654,266 A 8/1997 Chen et al.
5,700,670 A 12/1997 Yamagishi et al.
6,031,000 A 2/2000 Nissen et al.
6,207,856 B1 3/2001 Veech
6,217,915 B1 4/2001 Luchansky et al.
6,232,345 B1 5/2001 Hiraide et al.
6,316,038 B1 11/2001 Veech
6,323,237 B1 11/2001 Veech
6,380,244 B2 4/2002 Martin et al.
6,613,356 B1 9/2003 Vlahakos
6,706,756 B1 3/2004 Fitzpatrick et al.
6,835,750 B1 12/2004 Henderson
7,351,736 B2 4/2008 Veech
7,807,718 B2 10/2010 Hashim et al.
7,891,287 B2 2/2011 Miller
8,071,641 B2 12/2011 Weiss et al.
8,101,653 B2 1/2012 Veech
8,124,589 B2 2/2012 Henderson
8,344,896 B2 1/2013 Ozanne
8,426,468 B2 4/2013 Henderson
8,642,654 B2 2/2014 Clarke et al.
8,748,400 B2 6/2014 Henderson
9,138,420 B2 9/2015 D'Agostino et al.
9,186,340 B2 11/2015 Andrews et al.
9,211,275 B2 12/2015 Clarke et al.
9,435,566 B2 9/2016 Hill et al.
9,675,577 B2 6/2017 D'Agostino et al.
9,717,767 B2 8/2017 Carpenter et al.
9,795,580 B2 10/2017 Weeber et al.
9,808,481 B2 11/2017 Ritter et al.
9,925,164 B1 3/2018 Hashim
9,957,246 B2 5/2018 Stinchcomb et al.
10,022,409 B2 7/2018 Carpenter et al.
10,051,880 B2 8/2018 Clarke et al.
10,088,197 B2 10/2018 Hamagami et al.
10,245,242 B1 4/2019 Millet
10,245,243 B1 4/2019 Millet
10,278,961 B2 5/2019 Lowery et al.
10,292,592 B2 5/2019 Marshall et al.
10,292,952 B2 5/2019 Millet
10,407,331 B2 9/2019 Kamito et al.
10,512,615 B1 12/2019 Millet
10,588,876 B2 * 3/2020 Millet .................... A61P 3/10
10,588,877 B2 3/2020 Arnold
10,596,128 B2 3/2020 Millet
10,596,129 B2 3/2020 Millet
10,596,130 B2 3/2020 Millet
10,596,131 B2 3/2020 Millet
10,660,958 B2 5/2020 Clarke
10,736,861 B2 8/2020 Millet
10,792,269 B2 10/2020 Hashim
10,925,843 B2 2/2021 Millet
10,973,786 B2 4/2021 Millet
10,973,792 B2 * 4/2021 Millet .................... A61K 36/53
10,980,764 B1 4/2021 D'Agostino et al.
10,980,772 B2 4/2021 Millet
11,020,362 B2 6/2021 Millet
11,026,929 B2 6/2021 Lowery et al.
11,033,553 B2 6/2021 Millet
11,103,470 B2 8/2021 Millet
11,129,802 B2 9/2021 Millet
11,173,138 B2 11/2021 Lowery et al.
11,185,518 B2 11/2021 Millet
11,202,769 B2 12/2021 Millet
11,241,403 B2 2/2022 Millet
11,419,836 B2 * 8/2022 Millet .................... A61K 31/19
11,690,817 B2 7/2023 Millet
11,793,778 B2 10/2023 Millet
11,806,324 B2 11/2023 Millet
11,944,598 B2 4/2024 Millet
11,950,616 B2 4/2024 Millet
12,329,734 B2 * 6/2025 Millet .................. A61K 9/0053
2001/0014696 A1 8/2001 Veech
2001/0018866 A1 9/2001 Fischer
2001/0041736 A1 11/2001 Veech
2002/0013339 A1 1/2002 Martin et al.
2002/0124370 A1 9/2002 Deckert et al.
2003/0022937 A1 1/2003 Veech
2004/0126366 A1 7/2004 Kaddurah-Daouk et al.
2004/0138293 A1 7/2004 Werner et al.
2004/0266872 A1 12/2004 Veech
2005/0129783 A1 6/2005 Mccleary et al.
2005/0169968 A1 8/2005 Elmaleh et al.
2006/0165777 A1 7/2006 Solomon et al.
2006/0275253 A1 12/2006 Ushida et al.
2007/0029913 A1 2/2007 Chen
2007/0135376 A1 6/2007 Henderson
2007/0179197 A1 8/2007 Henderson
2008/0058416 A1 3/2008 Greenwood et al.
2008/0287372 A1 11/2008 Henderson
2009/0131475 A1 5/2009 Uesugi et al.
2009/0253781 A1 10/2009 Veech
2009/0306221 A1 12/2009 Guy et al.
2009/0325984 A1 12/2009 Costentin et al.
2010/0041751 A1 2/2010 Henderson
2010/0056631 A1 3/2010 Hisamura et al.
2010/0113494 A1 5/2010 Hu et al.
2010/0197758 A1 8/2010 Andrews et al.
2010/0210726 A1 8/2010 Kuriyama
2010/0298294 A1 11/2010 Clarke et al.
2011/0111049 A1 5/2011 Andrews et al.
2011/0237666 A1 9/2011 Clarke et al.
2011/0287114 A1 11/2011 Johnson
2012/0053240 A1 3/2012 Rathmacher et al.
2012/0071548 A1 3/2012 Veech
2012/0171165 A1 7/2012 Buck et al.
2012/0202891 A1 8/2012 Stinchcomb et al.
2013/0079406 A1 3/2013 Veech
2013/0337116 A1 12/2013 Petralia
2014/0256808 A1 9/2014 Henderson
2014/0329893 A1 11/2014 Veech
2014/0350105 A1 11/2014 D'Agostino et al.
2014/0352728 A1 12/2014 Svensson
2015/0018415 A1 1/2015 Veech
2015/0063140 A1 3/2015 Yi et al.
2015/0065571 A1 3/2015 Clarke et al.
2015/0132280 A1 5/2015 Lopez et al.
2015/0144074 A1 5/2015 Fujimoto et al.
2015/0320809 A1 11/2015 Carpenter et al.
2015/0363750 A1 12/2015 Svensson et al.
2016/0193173 A1 7/2016 Clarke et al.
2016/0256411 A1 9/2016 Aung-Din
2016/0263071 A1 9/2016 Borges et al.
2016/0272603 A1 9/2016 Kravchenko et al.
2017/0020844 A1 1/2017 Galinski
2017/0029650 A1 2/2017 Veling et al.
2017/0172969 A1 6/2017 D'Agostino et al.
2017/0258745 A1 9/2017 Millet
2017/0266148 A1 9/2017 D'Agostino et al.

(56) References Cited

U.S. PATENT DOCUMENTS

2017/0290792 A1 10/2017 Cavaleri
2017/0296501 A1 10/2017 Lowery et al.
2017/0296520 A1 10/2017 Lowery et al.
2017/0298339 A1 10/2017 Hanson et al.
2017/0304564 A1 10/2017 Dehaan et al.
2018/0020699 A1 1/2018 Steup
2018/0021274 A1 1/2018 Arnold
2018/0021281 A1 1/2018 Berger
2018/0055797 A1 3/2018 Llosa et al.
2018/0057846 A1 3/2018 Llosa et al.
2018/0195096 A1 7/2018 Veech et al.
2018/0214399 A1 8/2018 Spector et al.
2018/0238586 A1 8/2018 Sugatani et al.
2019/0099394 A1 4/2019 Ari et al.
2019/0151267 A1 5/2019 Millet
2019/0167613 A1 6/2019 Millet
2019/0167614 A1 6/2019 Millet
2019/0177673 A1 6/2019 Llosa et al.
2019/0183220 A1 6/2019 Takada
2019/0183820 A1 6/2019 Millet
2019/0183821 A1 6/2019 Millet
2019/0191755 A1 6/2019 Garvey et al.
2019/0209501 A1 7/2019 Tinsley et al.
2019/0255028 A1 8/2019 Lowery et al.
2019/0262293 A1 8/2019 Millet
2019/0313682 A1 10/2019 Nagel
2019/0321309 A1 10/2019 Millet
2020/0030266 A1 1/2020 Bradley et al.
2020/0061004 A1 2/2020 Millet
2020/0078973 A1 3/2020 Valeze et al.
2020/0129463 A1 4/2020 Lowery et al.
2020/0140371 A1 5/2020 Verdin et al.
2020/0170982 A1 6/2020 Millet
2020/0253909 A1 8/2020 Millet
2020/0268701 A1 8/2020 D'Agostino et al.
2021/0095867 A1 4/2021 Gururaja et al.
2021/0106168 A1 4/2021 Cingolani et al.
2021/0205241 A1 7/2021 Millet
2022/0133673 A1 5/2022 Millet
2022/0202760 A1 6/2022 Greenwood et al.
2023/0072854 A1 3/2023 Purpura et al.
2023/0115966 A1 4/2023 Wells et al.
2023/0201145 A1 6/2023 Millet
2024/0024265 A1 1/2024 Millet
2024/0197668 A1 6/2024 Millet
2025/0288550 A1* 9/2025 Millet .................... A61K 31/19

FOREIGN PATENT DOCUMENTS

CN 1256629 A 6/2000
CN 1347319 A 5/2002
CN 1104978 C 4/2003
CN 1184978 C 1/2005
CN 1972698 A 5/2007
CN 101674730 A 3/2010
CN 101678043 A 3/2010
CN 101969769 A 2/2011
CN 102164884 A 8/2011
CN 104224823 A 12/2014
CN 105050594 A 11/2015
CN 106038532 A 10/2016
CN 106459646 A 2/2017
CN 106858066 A 6/2017
CN 108253621 A 7/2018
CN 109480284 A 3/2019
CN 111655244 A 9/2020
CN 111867576 A 10/2020
CN 112262936 A 1/2021
DE 102017210992 A1 1/2019
EP 0008700 A1 3/1980
EP 1112711 A1 7/2001
EP 1178748 A1 2/2002
EP 1827412 A1 9/2007
EP 1915144 A2 4/2008
EP 2283834 A2 2/2011
EP 1755743 B1 4/2013
EP 2976073 A1 1/2016
EP 3094321 A1 11/2016
EP 3366173 A2 8/2018
EP 3446045 A1 2/2019
FR 2997302 A1 5/2014
GB 2391493 A 2/2004
ID 201701176 2/2017
JP 11-060434 A 3/1999
JP 2002-521330 A 7/2002
JP 2004-035417 A 2/2004
JP 5030553 B2 9/2012
JP 2015-042644 A 3/2015
JP 5690261 B2 3/2015
JP 2015-514104 A 5/2015
JP 2015-102323 A 6/2015
JP 2016-514725 A 5/2016
JP 2016-121128 A 7/2016
JP 2017-046688 A 3/2017
JP 2018-158897 A 10/2018
JP 2020-502652 A 1/2020
JP 2020-527583 A 9/2020
JP 2021-504476 A 2/2021
JP 2021-506294 A 2/2021
RU 2345546 C2 2/2009
WO 87/03808 A1 7/1987
WO 98/41200 A1 9/1998
WO 00/04895 A2 2/2000
WO 00/15216 A1 3/2000
WO 00/69315 A1 11/2000
WO 03/70823 A2 8/2003
WO 2005/077348 A1 8/2005
WO 2005/107724 A1 11/2005
WO 2006/029577 A1 3/2006
WO 2006/061624 A1 6/2006
WO 2007/115282 A2 10/2007
WO 2007/138322 A1 12/2007
WO 2008/005818 A1 1/2008
WO 2008/021394 A2 2/2008
WO 2008/024408 A2 2/2008
WO 2009/089144 A1 7/2009
WO 2010/021766 A1 2/2010
WO 2010/104595 A1 9/2010
WO 2011/101171 A1 8/2011
WO 2012/019295 A1 2/2012
WO 2012/024611 A1 2/2012
WO 2013/057506 A1 4/2013
WO 2013/150153 A1 10/2013
WO 2014/153415 A2 9/2014
WO 2014/153416 A1 9/2014
WO 2015/063140 A1 5/2015
WO 2015/071811 A1 5/2015
WO 2015/156865 A1 10/2015
WO 2016/123229 A1 8/2016
WO 2016/149687 A1 9/2016
WO 2017/156446 A1 9/2017
WO 2017/165443 A1 9/2017
WO 2017/165445 A1 9/2017
WO 2017/182664 A1 10/2017
WO 2017/184788 A1 10/2017
WO 2017/208217 A2 12/2017
WO 2018/055388 A1 3/2018
WO 2018/089863 A1 5/2018
WO 2018/114309 A1 6/2018
WO 2018/132189 A1 7/2018
WO 2018/175879 A1 9/2018
WO 2018/187324 A1 10/2018
WO 2018/187852 A1 10/2018
WO 2019/018683 A1 1/2019
WO 2019/108683 A1 6/2019
WO 2019/118624 A1 6/2019
WO 2019/200132 A1 10/2019
WO 2019/204148 A1 10/2019
WO 2019/237152 A1 12/2019
WO 2019/237185 A1 12/2019
WO 2020/041871 A1 3/2020

(56) References Cited

FOREIGN PATENT DOCUMENTS

| | | | |
|---|---|---|---|
| WO | 2020/092451 | A1 | 5/2020 |
| WO | 2021/178547 | A1 | 9/2021 |
| WO | 2022/040644 | A2 | 2/2022 |

OTHER PUBLICATIONS

Wang et al. Eucommiae cortex polysaccharides attenuate gut microbiota dysbiosis and neuroinflammation. in mice exposed to chronic unpredictable mild stress: Beneficial in ameliorating depressive-like behaviors, 2024, Journal of Affective Disorders, 334: 278-292 (Year: 2024).
Williams et al., "The Chemistry of the Ketogenic Diet: Updates and Opportunities in Organic Synthesis", Int J Mol Sci., May 15, 2021, vol. 22, No. 10, 5230, pp. 1-18.
WO2009045481, Pan et al. Published Apr. 9, 2009 Listed in this section as citation type "foreign" does not allow for any appropriate country code for "WO" documents.
Wu et al., "Medium-Chain Triglycerides in Infant Formulas and Their Relation to Plasma Ketone Body Concentrations," Pediatric Research, vol. 20, No. 4, (1986), pp. 338-341.
Yang Y. et al., Role of Adherent-Invasive *Escherichia coli* in Inflammatory Bowl Disease, Letters in Biotechnology, No. 06, Nov. 30, 2016.
Yang Yue et al., "Research on sarcopenic obesity", Chinese Journal of Modern Medicine, vol. 20, No. 3, Mar. 25, 2018, pp. 98-101.
Yang Zeyi, "Biochemistry of sports nutrition scientific research progress", Mar. 31, 2004, vol. 23, No. 2, pp. 158-165.
Zaleski, A. et al., Butyric acid in irritable bowel syndrome, 2013, Prz Gastroenterol, 8(6), 350-353 (Year: 2013).
Zeng Jing et al., "B-hydroxy-3-methyl—The clinical effects and mechanism", vol. 2, No. 2, Jun. 9, 2015, pp. 57-62.
A New Toy Measuring Blood Ketones. Diet Doctor, Aug. 21, 2012. Dowloaded Apr. 1, 2015. http://www.dietdoctor.com/a-new-toy-measuring-blood-ketoones.
Allendorfer et al., "Neuroimaging studies towards understanding the central effects of pharmacological cannabis products on patients with epilepsy", Epilepsy Behav, May 2017, vol. 70, pp. 349-354.
Amazon, "Perfect Keto Perform Pre Workout Powder—Bum Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild= 1 &keywords=ketone+pre+workout &qid= 1597938465&sr=8-9.
Anonymous: "Strawberry Pineapple Flavour Pre-Exertion Performance Optimizer", Mintel, Database accession No. 5661617, 2018, pp. 4.
Arendash et al. "Caffeine and Coffee as Therapeutics Against Alzheimer's Disease", Journal of Alzheimer's Disease 20, 2010, S117-S126.
Arnold, Instant Ketosis?, (2013), Aug. 4, 2013 (retrieved on Apr. 21, 2017), p. 1-3. Retrieved from the internet; URL: <http://patrickarnoldblog.com/instant-ketosis/. (Year: 2013).
Bala et al. Drug Invention Today. Jun. 1, 2018;10(6), 929-931.
Bastin et al., "Salt Slection and Optimisation Procedures for Pharmaceutical New Chemical Entities", American Chemical Society and the Royal Society of Chemistry, vol. 4, No. 5, 2000, pp. 427-435.
Blazquez et al. Journal of Neurochemistry, 1999, vol. 72 No. 4, pp. 1759-1768. (Year: 1999).
Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.
Clarke, et al., Kinetics, safety and tolerability of (R)-3-hydroxybutyl (R)-3-hydroxybutyrate in healthy adult subjects. Regul Toxicol Pharmacol. Aug. 2012; 63(3):401-8.
Craciun, S. et al. Microbial conversion of choline to trimethylamine requires a glycyl radical enzyme, 2012, PNAS, 109(52): 21307-21312 (Year: 2012).
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Daniells, Stephen, 'This is caffeine-evolved: Ingenious Ingredients co-founder talks up potential of paraxanthine,' Nov. 3, 2021, 2 pages, retrieved from https://www.nutraingredients-usa.com/Article/2021/11/03/This-is-caffeine-evolved-Ingenious-Ingredients-co-founder-talks-up-potential-of-paraxanthine accessed Feb. 7, 2023.
Database GNPD Mintel, Sep. 29, 2016, anonymous, "Blue Lemon Ice Advanced Formula", XP093048090, Database accession No. 4315637, pp. 3.
Decision to grant received for European Patent Application No. 17786592.0, mailed on Nov. 3, 2023, 2 pages.
Dedkova et al. "Role of B-hydroxybutyrate, its polymer poly-b-hydroxybutyrate and inorganic polyphosphate in mammalian health and disease", Frontiers in Physiology, Jul. 17, 2014, pp. 1-22.
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.
Energy Times—"Herbal Keto Support", Jan. 15, 2008 (5 pages).
European Search Report received for EP Patent Application No. 19880284.5, mailed on Jul. 12, 2022, 11 pages.
European Search Report received for EP Patent Application No. 20755289.4, mailed on Oct. 11, 2022, 7 pages.
European Search Report received for EP Patent Application No. 20755994.9, mailed on Sep. 21, 2022, 6 pages.
European Search Report received for EP Patent Application No. 20805593.9, mailed on Dec. 16, 2022, 9 pages.
European Search Report received for EP Patent Application No. 21750261.6, mailed on Feb. 2, 2024, 10 pages.
European Search Report received for EP Patent Application No. 21862356.9, mailed on Jul. 1, 2024, 10 pages.
Extended European Search Report pursuant to Rule 62 EPC (EPO Form 1507S) issued on Jan. 24, 2017 for corresponding European Patent Application No. 14770025.6.
Extended European Search Report received for EP Patent Application No. 19788264.0, mailed on Dec. 20, 2021, 11 pages.
Extended European Search Report received for EP Patent Application No. 20755770.3, mailed on Sep. 1, 2022, 7 pages.
First Examination Report for New Zealand Patent Application No. 711433 issued by the New Zealand Intellectual Property Office dated Mar. 10, 2016.
First Office Action issued by the Chinese State Intellectual Property Office on Nov. 4, 2016 for corresponding Chinese Patent Application No. 201480016818.0.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Hashim, Sami A., et al., "Ketone body therapy: from the ketogenic diet to the oral administration of ketone ester", Journal of Lipid Research, vol. 55, 2014.
Haywood A, Glass BD. Pharmaceutical excipients—where do we begin? Australian Prescriber. 2011; 34: 112-114.
Henderson, Samuel T. "Ketone Bodies as a Therapeutic for Alzheimer's Disease." Neurotherapeutics. Jul. 2008; 5(3):470-80.
Holscher, H. Dietary fiber and prebiotics and the gastrointestinal microbiota, 2017, Gut Microbes, 8(2): 172-184 (Year: 2017).
Holtzman et al., "Role of adenosine receptors in caffeine tolerance", J. Pharmacol. Exp. Ther., 1991 ; 256(1 ):62-68.
Huang Dexiang et al., "Clinical Intravenous Nutrition", Shanghai Medical University Press Jan. 31, 1994, pp. 121-124.

(56) References Cited

OTHER PUBLICATIONS

Ichim, T. et al., Experimental support for the effects of a probiotic/digestive enzyme supplement on serum cholesterol concentrations and the intestinal microbiome, 2016, Journal of Translational Medicine, 14(184), 1-9 (Year 2016).
Intention to grant received for European Patent Application No. 17786592.0, mailed on Jun. 27, 2023, 7 pages.
International Preliminary Report on Patentability received for PCT Patent Application No. PCT/US17/28465, mailed on Nov. 1, 2018, 7 pages.
International Preliminary Report on Patentability received for PCT Patent Application No. PCT/US17/28466, mailed on Nov. 1, 2018, 8 pages.
International Preliminary Report on Patentability received for PCT Patent Application No. PCT/US19/58676, mailed on May 14, 2021, 6 pages.
International Preliminary Report on Patentability received for PCT Patent Application No. PCT/US20/37289, mailed on Dec. 30, 2021, 6 pages.
International Preliminary Report on Patentability received for PCT Patent Application No. PCT/US2014/031237, mailed on Oct. 1, 2015, 8 pages.
International Preliminary Report on Patentability received for PCT Patent Application No. PCT/US2017/021886, mailed on Sep. 20, 2018, 9 pages.
International Preliminary Report on Patentability received for PCT Patent Application No. PCT/US2018/062093, mailed on Jun. 4, 2020, 6 pages.
International Preliminary Report on Patentability received for PCT Patent Application No. PCT/US2018/062096, mailed on Jul. 2, 2020, 8 pages.
International Preliminary Report on Patentability received for PCT Patent Application No. PCT/US2019/027214, mailed on Oct. 29, 2020, 09 pages.
Luis Villasenor, "Supplements and Ketogenic Diets—Facts and Myths", Retrieval from https://www.ketogains.com/2015/09/supplements-and-ketogenic-diets-facts-and-myths/, Sep. 18, 2015, pp. 15.
Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.
Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci. Jan. 28, 2019, vol. 30, No. 2, pp. 179-201.
Malo, M. S. et. al., Intestinal alkaline phosphatase preserves the normal homeostasis of gut microbiota, 2010, Gut, 59, 1476-1484 (Year: 2010).
Mangels D.R. et al, "Catechins as Potential Mediators of Cardiovascular Health", Translational Sciences, vol. 37, No. 5, May 1, 2017, pp. 757-763.
McFarland, L. Use of probiotics to correct dysbiosis of normal microbiota following disease or disruptive events: a systematic review, 2014, BMJ Open, 4(8): 1-18 (Year: 2014).
Murray, Andrew J., et al. "Novel ketone diet enhances physical and cognitive performance", The FASEB Journal, No. Dec. 30, 2016.
National Center for Biotechnology Information. PubChem Compound Summary for CID 441, 3-Hydroxybutyric acid, https://pubchem.ncbi.nlm.nih.gov/compound/3-Hydroxybutyric-acid. (Year: 2005).
Newman et al., "B-hydroxybutyrate: Much more than a metabolite", Diabetes Res Clin Pract., Nov. 2014.
Non-Final Rejection Mailed on Sep. 9, 2020 for U.S. Appl. No. 16/783,956.
Nova Max Plus Glucose and Ketone Testing with One Monitor. Downloaded Apr. 1, 2015. http://www.novacares.com/nova-max-plus/.
O'Mailey et al, Appl. Physiol. Nutr. Metab. 42: 1031-1035 (2017) Published at www.NRCRESEARCHPRESS.com/APNM on Jul. 27, 2017.
O'Meara, Cyndi, Changing Habits, Ketosis—Can we achieve it in a pill?, https://changinghabits. com.au/ketosis-can-we-achieve-it-in-a-pill/, 12 pages, (Jan. 13, 2017).
Office Action received for European Patent Application No. 17786592.0, mailed on Jun. 17, 2022, 7 pages.
Office Action received for European Patent Application No. 17786592.0, mailed on Sep. 25, 2020, 7 pages.
Office Action received for European Patent Application No. 19788264.0, mailed on Mar. 13, 2024, 5 pages.
Office Action received for European Patent Application No. 19880284.5, mailed on Nov. 9, 2023, 5 pages.
Office Action received for European Patent Application No. 20805593.9, mailed on Dec. 22, 2023, 7 pages.
Paraxanthine—Pubchem—2023 (Year: 2023).
Parker, Steve, "Ketogenic Mediterraanean Diet: Version 2.3," Nov. 23, 2010, pp. 1-3. (Year: 2010).
Partial supplementary European search report (EPO Form 1507US) issued by the European Patent Office on Sep. 21, 2016 for corresponding European Application No. 14770025.6.
Pete J Cox et al, "Acute nutritional ketosis: implications for exercise performance and metabolism," Extreme Physiology & Medicine, vol. 3, Issue 1, Dec. 1, 2014, pp. 1-9.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Rho et al. "Acetoacetate, Acetone, and Dibenzylamine (A Contaminant in L-(+)-Beta-Hydroxybutyrate) Exhibit Direct Anticonvulsant Actions In Vivo", Epilepsia, Raven Press Ltd, New York, US, vol. 43, No. 4, Apr. 1, 2002 (Apr. 1, 2002), pp. 358-361.
Riccio et al. The human gut microbiota is neither an organ nor a commensal, 2020, FEBS Letters, 594(20): 3262-3271 (Year: 2020).
Rich A.J., "Ketone Bodies as Substrates," Proceedings of the Nutrition Society (1990), vol. 49, 361-373.
Robson et al. Expert Opin. Drug Saf. (2011), vol. 10, pp. 675-685 (Year: 2011).
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Rogers GB et al. From gut dysbiosis to altered brain function and mental illness: mechanisms and pathways, 2016, Molecular Psychiatry, 21: 738-748 (Year: 2016).
Sajewicz et al. In Journal of Liquid Chromatography & Related Technologies, 33:1047-1057 (2010) (Year: 2010).
Sanchez, J. I. et al. Arabinoxylan-oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Sara, How do you know which product is right for you? How to choose exogenous ketones, https://ketosupplements.co.uk/how-to-choose-exogenous-ketones/, 10 pages, (Sep. 25, 2017).
Search Report and Written Opinion issued by the Intellectual Property Office of Singapore on Apr. 18, 2016 for corresponding Singapore Application No. 11201506780R.
Serum Ketones Test. MedlinePlus Medical Encyclopedia. Downloaded Apr. 1, 2015. http://www.nlm.nih.gov/medlineplus/ency/article/003498.htm.
Shigeno et al. in Biosci. Biotech. Biochem., 56(2), 320-323 (1992) (Year: 1992).

(56) References Cited

OTHER PUBLICATIONS

Short, Jay, Effects of a Ketone/Caffeine Supplement on Cycling and Cognitive Performance, Master's thesis, Ohio State University, 61 pages, (Jan. 1, 2017).
Slavin, J. Fiber and Prebiotics: Mechanisms and Health Benefits, 2013, Nutrients, 5: 1417-1425 (Year: 2013).
Sorensen et al. ("Simultaneous determination of B-hydroxybutyrate and B-hydroxy-B-methylbutyrate in human whole blood using hydrophilic interaction liquid chromatography electrospray tandem mass spectrometry", Clinical Biochemistry, 2013, vol. 46, pp. 1877-1883) (Year: 2013).
Stefan et al., "The Effects of Exogenous Beta-Hydroxybutyrate Supplementation on Metrics of Safety and Health", International Journal of Nutrition and Food Sciences, vol. 9, No. 6, Nov. 2020, pp. 154-162.
Stubbs et al., "On the Metabolism of Exogenous Ketones in Humans", frontiers in Physiology, vol. 8, 2017, 13 pages.
Supplementary European Search Report received for EP Patent Application No. 17786592.0, mailed on Nov. 25, 2019, 10 pages.
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
The Medical Republic, 2018, Sustained Release Sodium Butyrate Supplement Now Available to Support Management of GI Disorders, https://medicalrepublic.com.au/ sustained-release-sodium-butyrate-supplement-now-available-support-management-gi-disorders/15791; newly cited (Year: 2018).
Tisdale, "Reduction of weight loss and tumour size in a cachexia model by a high fat diet", British Journal of Cancer, Jul. 1987, vol. 56, p. 39-43.
Tsai et al., "Stereoselective effects of 3-hydroxybutyrate on glucose utilization of rat cardiomyocytes" life Sciences 78 (2006) pp. 1385-1391.
U.S. Appl. No. 62/324,798, filed Apr. 19, 2016, Lowery, priority document to U.S. Pat. No. 11,173,138.
Vandenberghe et al., "Caffeine intake increases plasma ketones: an acute metabolic study in humans", Canadian Journal of Physiology and Pharmacology, vol. 95, 2017, pp. 455-458.
International Preliminary Report on Patentability received for PCT Patent Application No. PCT/US2019/048357, mailed on Mar. 11, 2021, 08 pages.
International Preliminary Report on Patentability received for PCT Patent Application No. PCT/US2019/048364, mailed on Mar. 11, 2021, 7 pages.
International Preliminary Report on Patentability received for PCT Patent Application No. PCT/US2020/016952, mailed on Aug. 26, 2021, 7 pages.
International Preliminary Report on Patentability received for PCT Patent Application No. PCT/US2020/017552, mailed on Aug. 26, 2021, 7 pages.
International Preliminary Report on Patentability received for PCT Patent Application No. PCT/US2020/017555, mailed on Aug. 26, 2021, 7 pages.
International Preliminary Report on Patentability received for PCT Patent Application No. PCT/US2020/017556, mailed on Aug. 26, 2021, 7 pages.
International Preliminary Report on Patentability received for PCT Patent Application No. PCT/US2020/033159, mailed on Nov. 25, 2021, 6 pages.
International Preliminary Report on Patentability received for PCT Patent Application No. PCT/US2021/017078, mailed on Aug. 18, 2022, 7 pages.
International Preliminary Report on Patentability received for PCT Patent Application No. PCT/US2021/045186, mailed on Mar. 9, 2023, 7 pages.
International Preliminary Report on Patentability received for PCT Patent Application No. PCT/US2021/050302, mailed on Mar. 2, 2023, 8 pages.
International Preliminary Report on Patentability received for PCT Patent Application No. PCT/US2021/063559, mailed on Jul. 6, 2023, 6 pages.
International Preliminary Report on Patentability received for PCT Patent Application No. PCT/US2023/020407, mailed on Nov. 7, 2024, 7 pages.
International Search Report and Written Opinion issued in PCT/US19/48364 dated Nov. 15, 2019.
International Search Report and Written Opinion received for PCT Patent Application No. PCT/US17/28466, mailed on Jul. 5, 2017, 8 pages.
International Search Report and Written Opinion received for PCT Patent Application No. PCT/US19/58676, mailed on Jan. 16, 2020, 6 pages.
International Search Report and Written Opinion received for PCT Patent Application No. PCT/US2023/020407, mailed on Jul. 26, 2023, 10 pages.
International Search Report and Written Opinion received for PCT Patent Application No. PCT/US2023/020417, mailed on Jul. 21, 2023, 11 pages.
International Search Report and Written Opinion received for PCT Patent Application No. PCT/US17/28465, mailed on Jul. 5, 2017, 7 pages.
International Search Report and Written Opinion received for PCT Patent Application No. PCT/US20/017555, mailed on May 4, 2020, 8 pages.
International Search Report and Written Opinion received for PCT Patent Application No. PCT/US20/37289, mailed on Sep. 30, 2020, 8 pages.
International Search Report and Written Opinion received for PCT Patent Application No. PCT/US2014/031237, mailed on Jul. 15, 2014, 11 pages.
International Search Report and Written Opinion received for PCT Patent Application No. PCT/US2017/021886, mailed on Jun. 1, 2017, 15 pages.
International Search Report and Written Opinion received for PCT Patent Application No. PCT/US2018/062093, mailed on Feb. 1, 2019, 7 pages.
International Search Report and Written Opinion received for PCT Patent Application No. PCT/US2018/062096, mailed on Feb. 11, 2019, 13 pages.
International Search Report and Written Opinion received for PCT Patent Application No. PCT/US2019/027214, mailed on Jun. 25, 2019, 14 pages.
International Search Report and Written Opinion received for PCT Patent Application No. PCT/US2019/048357, mailed on Nov. 18, 2019, 13 pages.
International Search Report and Written Opinion received for PCT Patent Application No. PCT/US2020/016952, mailed on Apr. 22, 2020, 9 pages.
International Search Report and Written Opinion received for PCT Patent Application No. PCT/US2020/017552, mailed on May 4, 2020, 9 pages.
International Search Report and Written Opinion received for PCT Patent Application No. PCT/US2020/017556, mailed on May 4, 2020, 12 pages.
International Search Report and Written Opinion received for PCT Patent Application No. PCT/US2020/033159, mailed on Aug. 12, 2020, 9 pages.
International Search Report and Written Opinion received for PCT Patent Application No. PCT/US2021/063559, mailed on Mar. 18, 2022, 9 pages.
International Search Report and Written Opinion received for PCT Patent Application No. PCT/US21/045186, mailed on Nov. 22, 2021, 10 pages.
International Search Report and Written Opinion received for PCT Patent Application No. PCT/US21/17078, mailed on Apr. 23, 2021, 9 pages.
International Search Report and Written Opinion received for PCT Patent Application No. PCT/US22/36030, mailed on Oct. 7, 2022, 7 pages.

(56) References Cited

OTHER PUBLICATIONS

International Search Report and Written Opinion received for PCT Patent Application No. PCT/US22/49036, mailed on Mar. 8, 2023, 9 pages.
Invitation to Respond to Written Opinion issued by the Intellectual Property Office of Singapore dated Dec. 28, 2016 for corresponding Singapore Patent Application No. 11201506780R.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Karppanen, H., et al, "Why and how to implement sodium, potassium, calcium, and magnesium changes in food items and diets?" J. Human Hypertension (2005), vol. 19, pp. S10-S19.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Kesl, et al., "Effects of exogenous ketone supplementation on blood ketone, glucose, triglyceride, and lipoprotein levels in Sprague-Dawley rats", Nutrition & Metabolism (2016).
Kim Do Young et al., "Ketone bodies are protective against oxidative stress in neocortical neurons," Journal of Neurochemistry, vol. 101, Issue 5, Jun. 1, 2007, pp. 1316-1326.
Kirsch, JR et al. "Butanediol Induced Ketosis Increases Tolerance to Hypoxia in the Mouse." Stroke. 1980. vol. 11, No. 5, pp. 506-513.
Kossoff, Eric H. et al. "Optimal Clinical Management of Children Receiving the Ketogenic Diet: Recommendations of the International Ketogenic Diet Study Group." Epilepsia, Feb. 2009; 50(2):304-17. Epub Sep. 23, 2008.
Krotkiewski, "Value of VLCD Supplementation with Medium Chain Triglycerides", Int J Obes Relat Metab Disord, Sep. 2001, 25 (9), pp. 1393-1400.
Lang Chaochun, "Healthy fitness and exercise prescription", Nov. 30, 2013, p. 201.
Lannotti et al., "Effects of non-euphoric plant cannabinoids on muscle quality and performance of dystrophic mdx mice", Br J Pharmacol, May 2019, vol. 176, No. 10, pp. 1568-1584.
Lile et al. Drug Alcohol Depend. 2012, 122 (1-2), 61-69.
Lonza, Duocap Capsules, Feb. 16, 2018, https ://web .archive .org/web/20180216001656/https://www.capsugel.com/consumer-health-nutrition-products/duocap-capsules (Year: 2018).

* cited by examiner

S-β-HYDROXYBUTYRATE ESTERS FOR IMPROVING METABOLIC FUNCTION

CROSS-REFERENCE TO RELATED APPLICATIONS

This Application is a continuation-in-part of U.S. application Ser. No. 19/221,260, filed May 28, 2025, which is a continuation of U.S. application Ser. No. 18/592,262, filed Feb. 29, 2024, now U.S. Pat. No. 12,329,734, which is a continuation-in-part of U.S. application Ser. No. 18/218,519, filed Jul. 5, 2023, now U.S. Pat. No. 11,944,598, which is a continuation-in-part of U.S. patent application Ser. No. 17/555,724, filed Dec. 20, 2021, now U.S. Pat. No. 11,786,499, which is a continuation of U.S. patent application Ser. No. 17/130,498, filed Dec. 22, 2020, now U.S. Pat. No. 11,202,769, which is a continuation-in-part of U.S. patent application Ser. No. 16/783,886, filed Feb. 6, 2020, now U.S. Pat. No. 11,185,518, which is a continuation-in-part of U.S. patent application Ser. No. 16/272,192, filed Feb. 11, 2019, now U.S. Pat. No. 10,596,130, which is a continuation-in-part of U.S. patent application Ser. No. 16/224,485, filed Dec. 18, 2018, now U.S. Pat. No. 10,596,128, which is a division of U.S. patent application Ser. No. 15/936,849, filed Mar. 27, 2018, now U.S. Pat. No. 10,245,243, which claims the benefit of U.S. Provisional Application No. 62/607,578, filed Dec. 19, 2017, which are incorporated herein by reference in their entirety.

This Application is also a continuation-in-part of U.S. application Ser. No. 19/096,389, filed Mar. 31, 2025, which is a continuation of U.S. application Ser. No. 18/977,541, filed Dec. 11, 2024, now U.S. Pat. No. 12,350,243, which is a continuation of U.S. application Ser. No. 18/219,556, filed Jul. 7, 2023, now U.S. Pat. No. 12,251,362, which is a continuation of U.S. patent application Ser. No. 17/367,206, filed Jul. 2, 2021, now U.S. Pat. No. 12,109,182, which is a continuation-in-part of U.S. patent application Ser. No. 15/491,924, filed Apr. 19, 2017, now U.S. Pat. No. 11,173,138, which claims the benefit of U.S. Provisional Application No. 62/324,798, filed Apr. 19, 2016, which are incorporated herein by reference in their entirety.

BACKGROUND

1. Field of the Invention

The invention relates to S-beta-hydroxybutyrate esters, non-racemic beta-hydroxybutyrate esters enriched with S-beta-hydroxybutyrate esters relative to R-beta-hydroxybutyrate esters, and compositions and methods for improving metabolic function.

2. Related Technology

In periods of fasting, extreme exercise, and/or low carbohydrate consumption, glucose and glycogen stores in the body are rapidly used and can become quickly depleted. Failure to replenish glucose stores as they become depleted causes the body to metabolically shift to the creation and use of ketone bodies for energy ("ketosis"). Ketone bodies can be used by cells of the body as a fuel to satisfy the body's energy needs, including the brain and heart. During prolonged fasting, for example, blood ketone levels can increase to 2-3 mmol/L or more. It is conventionally understood that when blood ketones rise above 0.5 mmol/L, the heart, brain and peripheral tissues are using ketone bodies (e.g., beta-hydroxybutyrate and acetoacetate) as the primary fuel source. This condition is referred to as ketosis. At blood levels between 1.0 mmol/L and 3.0 mmol/L the condition is called "nutritional ketosis."

Upon transitioning into ketosis, or in other words, during ketogenic metabolism in the liver, the body uses dietary and bodily fats as a primary energy source. Consequently, once in ketosis, one can induce loss of body fat by controlling dietary fat intake and maintaining low carbohydrate intake and blood level to sustain ketosis.

During ketosis, the body is in ketogenesis and essentially burning fat for its primary fuel. The body cleaves fats into fatty acids and glycerol and transforms fatty acids into acetyl COA molecules, which are then eventually transformed through ketogenesis into the water-soluble ketone bodies beta-hydroxybutyrate (i.e., "β-hydroxybutyrate" or "BHB"), acetoacetate (also known as acetylacetonate), and acetone in the liver. Beta-hydroxybutyrate and acetoacetate are the primary ketone bodies used by the body for energy while acetone is removed and expelled as a by-product of ketogenesis.

The metabolism of ketone bodies is associated with several beneficial effects, including anticonvulsant effects, enhanced brain metabolism, neuroprotection, muscle sparing properties, and improved cognitive and physical performance. Science-based improvements in efficiency of cellular metabolism, managed through ketone supplementation, can have beneficial impacts on physical, cognitive health, and psychological health, and a long-term impact on health with respect to common avoidable diseases such as obesity, cardiovascular disease, neurodegenerative diseases, diabetes, and cancer.

Despite the many health advantages of pursuing a ketogenic diet or lifestyle and maintaining a state of nutritional ketosis, there remain significant barriers to pursuing and maintaining a ketogenic state. One of these barriers is the difficulty of transitioning into a ketogenic state. The fastest endogenous way to entering ketosis through depleting glucose stores in the body is by fasting combined with exercise. This is physically and emotionally demanding and is extremely challenging even for the most motivated and disciplined.

Additionally, the transition into ketosis is often accompanied by hypoglycemia, which can cause lethargy and light-headedness in many, resulting in an uncomfortable physiological and mental state commonly referred to as the "low-carb flu." In addition, many people experience a down regulation in their metabolism as the body naturally goes into an "energy-saving" mode. Some suggest that these transitory symptoms may last as long as two to three weeks. During this transition period, if a subject consumes a meal or snack containing carbohydrates above the restrictive amount, there is an immediate termination of ketogenisis, exiting the body from its state of ketosis, as the body shifts back to glucose utilization for its primary fuel and the transition into ketosis must begin anew.

If a subject is successful in establishing ketosis, the act of sustaining ketosis is likewise difficult, if not more difficult, due to the need to maintain a rigid dietary ratio of carbohydrates and protein to fats. It is further complicated by the disruption of normal electrolyte balances that often occurs when transitioning into and maintaining a ketogenic state. The depletion and lowering of glycogen stores in the liver and muscles lessens the ability of the body to retain water, leading to more frequent urination, and accordingly, a greater loss of electrolytes. Further, the drop in insulin levels caused by ketosis affects the rate at which certain electrolytes are extracted by the kidneys, additionally lowering electrolyte levels in the body. Negative effects of electrolyte imbalance include muscle aches, spasms, twitches and weakness, restlessness, anxiety, frequent headaches, feeling very thirsty, insomnia, fever, heart palpitations or irregular heartbeats, digestive issues such as cramps, constipation or diarrhea, confusion and trouble concentrating, bone disorders, joint pain, blood pressure changes, changes in appetite or body weight, fatigue (including chronic fatigue syndrome), numbness in joints, and dizziness, especially when standing up suddenly.

Some compositions used to promote ketosis in a mammal include a racemic mixture of beta-hydroxybutyrate (RS-beta-hydroxybutyrate or DL-beta-hydroxybutyrate). Other compositions, such as those disclosed in U.S. Patent Publication No. 2017/0296501 to Lowery et al., contain the endogenous form of beta-hydroxybutyrate, or R-beta-hydroxybutyrate, while Lowery et al. discourage use of the non-endogenous enantiomer, or S-beta-hydroxybutyrate. Others, such as those disclosed in U.S. Pat. No. 8,642,654 to Clarke et al., consist mostly or entirely of a single beta-hydroxybutyrate ester (3R)-hydroxybutyl (3R)-hydroxybutyrate. Other enantiomers, such as (3R)-hydroxybutyl (3S)-hydroxybutyrate, (3S)-hydroxybutyl (3R)-hydroxybutyrate, and (3S)-hydroxybutyl (3S)-hydroxybutyrate, are mostly or entirely omitted. The omission of enantiomers that are not the endogenous form of beta-hydroxybutyrate is based on the view that S-beta-hydroxybutyrate (aka (3S)-hydroxybutyrate) is ineffective or even harmful.

SUMMARY

Disclosed herein are compositions and methods for improving metabolic function in a subject, including improving brain, heart, and other metabolic functions in a subject. Example compositions include S-beta-hydroxybutyrate compounds and non-racemic mixtures of S-beta-hydroxybutyrate and R-beta-hydroxybutyrate, wherein the non-racemic mixtures are enriched with the S-beta-hydroxybutyrate enantiomer relative to the R-beta-hydroxybutyrate enantiomer, such as by including 51% to 99.5% by enantiomeric equivalents of the S-beta-hydroxybutyrate enantiomer and 49.5% to 0.5% by enantiomeric equivalents of the R-beta-hydroxybutyrate enantiomer. Of particular interest are beta-hydroxybutyrate esters, including esters of optically pure S-beta-hydroxybutyrate and non-racemic mixtures enriched with S-beta-hydroxybutyrate.

As will be discussed more fully below, administering S-beta-hydroxybutyrate esters in enantiomerically pure or enriched form has been found to be particularly effective in improving metabolic function in a subject. In some embodiments, S-beta-hydroxybutyrate esters, either administered to the subject in optically pure form or as a non-racemic mixture enriched with S-beta-hydroxybutyrate relative to R-beta-hydroxybutyrate, is effective to provide energy to the brain, heart, organs, and peripheral tissues, as well as improving metabolic function in other ways. In addition, S-beta-hydroxybutyrate esters are particularly effective in dilating arteries, which reduces blood pressure and systemic vascular resistance and increases cardiac output.

It has been found that administering about 0.5 g to 30 g, such as about 2 g to about 25 g, preferably about 5 g to about 20 g, more preferably about 7.5 g to about 17.5 g, and most preferably about 10 g to about 15 g, of at least one S-beta-hydroxybutyrate ester in enantiomerically pure or enriched form can improve heart, brain, and other metabolic functions in a subject. Optically pure S-beta-hydroxybutyrate esters have been found to be particularly effective in improving heart, brain, and other metabolic functions, although non-racemic mixtures enriched with S-beta-hydroxybutyrate ester relative to R-beta-hydroxybutyrate ester are also effective if given in high enough doses to ensure that a sufficient quantity of S-beta-hydroxybutyrate ester is administered to improve heart, brain, and other metabolic functions, which can vary by individual, weight, age, sex, health, metabolism, and other factors.

Non-racemic mixtures of S-beta-hydroxybutyrate and R-beta-hydroxybutyrate contain more of the S-beta-hydroxybutyrate enantiomer than the endogenous form (R-enantiomer) produced by a mammal and can provide a more controlled and sustained ketogenic effect compared to a racemic mixture and/or compositions that contain optically pure R-beta-hydroxybutyrate or non-racemic mixtures enriched with the R-enantiomer. Because R-beta-hydroxybutyrate is endogenously produced by a mammal during ketosis, administering the R-beta-hydroxybutyrate enantiomer to a subject provides a quantity that can be immediately utilized by the body, such as for producing energy (e.g., as an alternative energy source to glucose), including energy used by the heart, brain, and peripheral tissues. However, this effect is modulated and extended when the S-enantiomer is the predominant component. S-beta-hydroxybutyrate also provides its own unique benefits, such as signaling, as described herein.

Contrary to compositions that are deliberately enriched with the R-enantiomer or that minimize or eliminate S-beta-hydroxybutyrate altogether, non-racemic mixtures disclosed herein are enriched with S-beta-hydroxybutyrate, which is typically not endogenously produced by mammals in appreciable quantities, in order to produce one or more desired effects in the mammal, as discussed herein.

In addition, while conventional compositions typically contain polymer, oligomer, ester, or salt forms of beta-hydroxybutyrate, pure S-beta-hydroxybutyrate compounds and non-racemic mixtures enriched with S-beta-hydroxybutyrate relative to R-beta-hydroxybutyrate can include the free acid form of S-beta-hydroxybutyrate and optionally R-beta-hydroxybutyrate. For example, the S-beta-hydroxybutyrate compound or non-racemic mixture may contain one or more salts or esters of optically pure S-beta-hydroxybutyrate, or a non-racemic mixture of S-beta-hydroxybutyrate and R-beta-hydroxybutyrate salts and/or esters in combination with S-beta-hydroxybutyric acid, and optionally R-beta-hydroxybutyric acid. Combining beta-hydroxybutyric acid with one or more beta-hydroxybutyrate salts or esters is beneficial because it reduces electrolyte load, increases absorption rate, improves taste, facilitates easier formulation, and reduces the need to add citric acid or other edible acids to obtain a composition having neutral or acidic pH.

In some embodiments, the compositions disclosed herein can be used in a method for increasing ketone body level in a subject, including promoting and/or sustaining ketosis in a subject, comprising administering to a subject in need thereof a nutritionally or pharmaceutically effective amount of one or more compositions disclosed herein. Examples of beneficial effects of increased ketone body level in a subject, particularly by administering S-beta-hydroxybutyrate, include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, improved body composition, increased energy used by the heart, and improved vascular system. The effects which benefit the vascular system can contribute to improving heart function in a subject, such as by dilating the arteries, which reduces blood pressure and systemic vascular resistance and increases cardiac output.

In some embodiments, administering pure S-beta-hydroxybutyrate or a non-racemic mixture of S-beta-hydroxybutyrate and R-beta-hydroxybutyrate in the enantiomeric ratios or percentages disclosed herein provide one or more of: increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

In some embodiments, the composition may include a nutritionally or pharmaceutically acceptable carrier.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

Disclosed herein are compositions and methods for administering S-beta-hydroxybutyrate in enantiomerically pure or enriched form to improve metabolic function in a subject in need thereof. Of particular interest are S-beta-hydroxybutyrate esters, which have been found to improve brain, heart, organ, and other metabolic functions.

Administering S-beta-hydroxybutyrate in enantiomerically pure or enriched form has been found to improve brain, heart, organ, and other metabolic functions in a subject. Optically pure S-beta-hydroxybutyrate has been found to be most effective in improving brain, heart, organ, and other metabolic functions, although non-racemic mixtures enriched with S-beta-hydroxybutyrate relative to R-beta-hydroxybutyrate are also effective if given in high enough doses to ensure that a sufficient quantity of S-beta-hydroxybutyrate is administered to improve brain, heart, organ, and other metabolic functions, which can vary by individual, weight, age, sex, health, and other factors.

I. DEFINITIONS

The compound "beta-hydroxybutyrate," also known as β-hydroxybutyrate, 3-hydroxybutyrate, βHB, or BHB, is the deprotonated form of beta-hydroxybutyric acid, which is a hydroxycarboxylic acid having the general formula $CH_3CH_2OHCH_2COOH$. The deprotonated form present at typical biological pH levels is $CH_3CH_2OHCH_2COO^-$. The general chemical structure shown below represents beta-hydroxybutyrate compounds that may be utilized in the disclosed compositions:

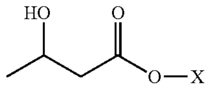

where,

X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

In some cases, the composition can include a mixture of one or more beta-hydroxybutyrate salts and beta-hydroxybutyric acid(s). Providing S-beta-hydroxybutyrate in its acid form can be beneficial because of its much quicker absorption response time compared to the salt form. Nonetheless, even though the acid form by itself is a liquid with extremely low pH and unpalatable taste, when made or combined with the salt form(s) and where the amount of beta-hydroxybutyric acid is small relative to the salt form(s), the composition can still form a solid, powder or other form typical of the salt form(s). In such case, the combined salt and acid form of BHB has acceptable pH and taste. BHB compositions that include both salt and acid forms have advantages, such as increased absorption rate, increased bioavailability, lower electrolyte load, case of manufacture, significantly improved taste, and reduced need for citric acid or other edible acids to obtain a composition with neutral or acidic pH. It will be appreciated that beneficial effects can also be provided using a mixture of BHB salt(s) and/or ester(s) and the acid form(s) of BHB.

The term "free beta-hydroxybutyric acid" means the sum of non-deprotonated and deprotonated beta-hydroxybutyric acid molecules not paired with a cation other than hydronium. A deprotonated beta-hydroxybutyric acid molecule generally means a molecule that has released a proton to form a hydronium ion ($H_3O+$) and a beta-hydroxybutyrate anion (e.g., dissolved in water).

Free beta-hydroxybutyric acid molecules are typically not deprotonated to any significant degree when contained in a beta-hydroxybutyrate mixed salt-acid composition in dry powder or other solid form. In such cases, the fractional amount of free beta-hydroxybutyric acid in a beta-hydroxybutyrate mixed salt-acid composition on a weight basis is the weight of free beta-hydroxybutyric acid divided by the combined weight of free beta-hydroxybutyric acid and beta-hydroxybutyrate salt(s). On a molar basis, the fractional amount of free beta-hydroxybutyric acid in an beta-hydroxybutyrate mixed salt-acid composition are the molar equivalents of free beta-hydroxybutyric acid divided by the sum of molar equivalents of free beta-hydroxybutyric acid and beta-hydroxybutyrate anions provided by the beta-hydroxybutyrate salt(s).

When dissolved in water, a portion of the beta-hydroxybutyric acid will typically dissociate into beta-hydroxybutyrate anions and hydronium ions ($H_3O+$). As a result, beta-hydroxybutyric acid molecules can exchange protons and cations with dissolved beta-hydroxybutyrate salts. For purposes of defining the relative amounts of beta-hydroxybutyric acid and beta-hydroxybutyrate salt(s) in a beta-hydroxybutyrate mixed salt-acid composition, dissociation of beta-hydroxybutyric acid molecules and the exchange of protons and cations is not understood as changing the molar ratio of free beta-hydroxybutyric acid relative to beta-hydroxybutyrate anions from the beta-hydroxybutyrate salt(s). The total quantity of free beta-hydroxybutyric acid molecules in solution equals the total equivalents of dissolved beta-hydroxybutyric acid molecules that are not deprotonated and beta-hydroxybutyrate anions formed by deprotonation of beta-hydroxybutyric acid molecules, minus the equivalents of cations other than hydronium ions.

Stated another way, the total molar equivalents of beta-hydroxybutyric acid in solution, whether or not deprotonated, is understood to be the difference between (i) the sum of molar equivalents of non-deprotonated beta-hydroxybutyric acid molecules and total molar equivalents of beta-hydroxybutyrate anions in solution (from all sources) and (ii) the total molar equivalents of cationic charge provided by cations from any beta-hydroxybutyrate salt compounds (which equals the total molar equivalents of beta-hydroxybutyrate anions provided by the beta-hydroxybutyrate salt(s)). Alkali metal cations such as sodium and potassium provide 1 mole of cationic charge per mole of metal cations. Alkaline earth metal cations such as magnesium and calcium, on the other hand, provide 2 moles of cationic charge per mole of metal cations. 1 mole of deprotonated beta-hydroxybutyric acid molecules provide 1 mole of anionic charge and one mole of cationic charge. Thus, salts of calcium and magnesium provide 2 moles of beta-hydroxybutyrate per mole of salt, while salts of sodium and potassium provide 1 mole of beta-hydroxybutyrate per mole of salt.

In view of the foregoing, the molar fraction of beta-hydroxybutyric acid in solution in relation to total moles of beta-hydroxybutyrate molecules from the beta-hydroxybutyrate mixed salt-acid composition in solution is [(i)-(ii)÷(i)], and the molar fraction of beta-hydroxybutyrate molecules from the beta-hydroxybutyrate salt(s)) in solution is [(ii)÷(i)]. Multiplying the molar fraction of each by 100 gives the percentage of each in solution.

By way of example, if 100 molar equivalents of beta-hydroxybutyrate mixed salt-acid composition in a dry powdered state contained 5% of free non-deprotonated beta-hydroxybutyric acid and 95% beta-hydroxybutyrate salt(s) on a molar basis, there would be essentially 5 molar equivalents of beta-hydroxybutyric acid molecules and 95 molar equivalents of beta-hydroxybutyrate anions. When there is sufficient water to dissolve the beta-hydroxybutyrate salt(s), and if a portion of the beta-hydroxybutyric acid molecules were deprotonated, the molar equivalents of non-deprotonated beta-hydroxybutyric acid would be less than 5, and the molar equivalents of beta-hydroxybutyrate anions would be greater than 95. The extent of deprotonation of beta-hydroxybutyric acid in solution is related to solution pH.

Whether beta-hydroxybutyrate is the S- or R-enantiomer depends on the tetrahedral orientation of the hydroxy (or oxy group in the case of an ester) on the 3-carbon (beta-carbon) in relationship to the planar carboxyl group.

Beta-hydroxybutyrate, typically R-beta-hydroxybutyrate, which is the endogenous form, can be utilized by a patient's body as a fuel source during instances of low glucose levels in the subject or when a patient's body is supplemented with a usable form of beta-hydroxybutyrate. Beta-hydroxybutyrate is commonly referred to as a "ketone body".

As used herein, a "ketogenic composition" is formulated to increase ketone body level in a subject, including inducing and/or sustaining a state of elevated ketone bodies at a desired level, such as ketosis, in a subject to which it is administered.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

The term "unit dose" refers to a dosage form that is configured to deliver a specified quantity or dose of composition or component thereof. Example dosage forms include, but are not limited to, tablets, capsules, powders, food products, food additives, beverages (such as flavored, vitamin fortified, or non-alcoholic), beverage additives (such as flavored, vitamin fortified, or non-alcoholic S-BHB concentrates), candies, suckers, pastilles, food supplements, dietetically acceptable sprays (such as flavored mouth spray), injectables (such as an alcohol-free injectable), and suppositories. Such dosage forms may be configured to provide a full unit dose or fraction thereof (e.g., ½, ⅓, or ¼ of a unit dose).

Another dosage form that can be used to provide a unit dose of composition or component thereof is a unit dose measuring device, such as a cup, scoop, syringe, dropper, spoon, spatula, or colonic irrigation device, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, liquid squeeze bottle with integrated measuring cup (or other unit dose measuring device), or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing a composition as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, may be attached to the bulk container, may be integrally formed with the bulk container, may be prepackaged with the bulk container within a larger package, or may be provided by the seller or manufacture for use with one or multiple bulk containers.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as spoons, spatulas, cups, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

"Ketosis" as used herein refers to a subject having blood ketone levels within the range of about 0.5 mmol/L and about 16 mmol/L in a subject. Ketosis may improve mitochondrial function, decrease reactive oxygen species production, reduce inflammation and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

The term "short chain triglycerides" (SCT) refers to molecules having a glycerol backbone attached to three medium chain fatty acids. Short chain fatty acids can range from 2 to 5 carbon atoms in length. Exemplary short chain fatty acids are acetic acid, propionic acid, butyric acid, isobutyric acid, valeric acid, and isovaleric acid. An example SCT is tributyrin.

The term "medium chain triglycerides" (MCT) refers to molecules having a glycerol backbone attached to three medium chain fatty acids. Medium chain fatty acids can range from 6 to 12 carbon atoms in length, and more likely 8 to 10 carbon atoms in length. Exemplary fatty acids are caprylic acid, also known as octanoic acid, comprising 8 carbon molecules, and capric acid, also known as decanoic acid, comprising 10 carbon molecules. MCTs, medium chain fatty acids, and mono- and di-glycerides are ketone body precursors that can provide an additional source for the production of ketone bodies independent of beta-hydroxybutyrate.

The term "long chain triglycerides" (LCT) refers to molecules having a glycerol backbone attached to three medium chain fatty acids. Long chain fatty acids can be greater than 12 carbon atoms in length.

The term "administration" or "administering" is used herein to describe the process in which the disclosed compositions are delivered to a subject. The composition may be administered in various ways including oral, intragastric, and parenteral (referring to intravenous and intra-arterial and other appropriate parenteral routes), among others.

II. S-BETA-HYDROXYBUTYRATE COMPOUNDS AND NON-RACEMIC MIXTURES ENRICHED WITH S-BETA-HYDROXYBUTYRATE

Compositions for increasing ketone body level in a subject, including improving brain, heart, organ, and other metabolic functions and/or modulating ketosis, comprise optically pure (100%) S-beta-hydroxybutyrate or a non-racemic mixture of S-beta-hydroxybutyrate enriched with the S-enantiomer (i.e., more than 50% and less than 100% by enantiomeric equivalents of S-beta-hydroxybutyrate and less than 50% and more than 0% by enantiomeric equivalents of R-beta-hydroxybutyrate).

In some embodiments, non-racemic mixtures of S-beta-hydroxybutyrate and R-beta-hydroxybutyrate contain from 50.5% to 99.5%, 51% to 99%, 52% to 98%, 53% to 97%, 55% to 96%, 57% to 93%, 60% to 90%, or 65% to 85% by enantiomeric equivalents of the S-beta-hydroxybutyrate enantiomer and 49.5% to 0.5%, 49% to 1%, 48% to 2%, 47% to 3%, 45% to 4%, 3% to 7%, 40% to 10%, or 35% to 15% by enantiomeric equivalents of the R-beta-hydroxybutyrate enantiomer.

Non-racemic mixtures of S-beta-hydroxybutyrate and R-beta-hydroxybutyrate contain more S-beta-hydroxybutyrate than the endogenous form produced by a mammal, which is R-beta-hydroxybutyrate, in order to provide for more controlled, gradual, extended, and/or modulated ketogenic effect compared to either a racemic mixture or composition enriched with the R-beta-hydroxybutyrate enantiomer. Because the R-beta-hydroxybutyrate enantiomer is endogenously produced by a mammal during ketosis, administering the R-beta-hydroxybutyrate enantiomer to a subject provides an additional quantity and/or increased blood plasma level that can be immediately utilized by the body, such as for producing energy (e.g., as an alternative energy source to glucose). However, this effect is modulated and extended due to the S-enantiomer being the predominant component.

Contrary to compositions that deliberately minimize or eliminate S-beta-hydroxybutyrate, the non-racemic mixture contains a majority quantity of the S-beta-hydroxybutyrate enantiomer, which is not endogenously produced by a mammal, in order to produce one or more desired effects in the mammal. For example, administering S-beta-hydroxybutyrate along with R-beta-hydroxybutyrate can result in at least one of: (1) increased endogenous production of R-beta-hydroxybutyrate and acetoacetate; (2) endogenous conversion of the S-beta-hydroxybutyrate into one or both of R-beta-hydroxybutyrate and acetoacetate; (3) endogenous conversion of the S-beta-hydroxybutyrate into fatty acids and sterols; (4) prolonged ketosis; (5) metabolism of the S-beta-hydroxybutyrate independent of conversion to R-beta-hydroxybutyrate and/or acetoacetate; (6) increased fetal development; (7) increased growth years; (8) reduced endogenous production of acetone during ketosis; (9) signaling by the S-beta-hydroxybutyrate that modulates metabolism of R-beta-hydroxybutyrate and glucose; (10) antioxidant activity; (11) production of acetyl-CoA; and (12) improving heart function.

Optically pure S-beta-hydroxybutyrate or a non-racemic mixture of S-beta-hydroxybutyrate and R-beta-hydroxybutyrate can be used, for example, to produce one or more desired effects in the subject, including but not limited to, appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, improved body composition, or improved metabolic function, including improved brain, heart, organ, and other metabolic functions.

In some embodiments, the composition may include a nutritionally or pharmaceutically acceptable carrier.

S-beta-hydroxybutyrate and R-beta-hydroxybutyrate can be provided in various forms, such as salts and/or esters and/or free acid form(s). The percent of enantiomer equivalents of each of the S-beta-hydroxybutyrate and R-beta-hydroxybutyrate is defined by molar equivalents of either S-beta-hydroxybutyrate or R-beta-hydroxybutyrate divided by total combined molar equivalents of S-beta-hydroxybutyrate and R-beta-hydroxybutyrate. The amounts of any cations forming salts and/or alcohols forming esters are excluded and do not count in determining the percent of enantiomeric equivalents of each of S-beta-hydroxybutyrate and R-beta-hydroxybutyrate. For example, the weight contributions of cations, alcohols, or complexing agents can be factored in so as to not tip the scale relative to enantiomeric equivalents of R-BHB and S-BHB.

In some embodiments, optically pure S-beta-hydroxybutyrate or a non-racemic mixture of S-beta-hydroxybutyrate and R-beta-hydroxybutyrate is provided in a composition that includes a dietetically or pharmaceutically acceptable carrier. Examples include powders, liquids, tablets, capsules, food products, food additives, beverages, vitamin fortified beverages, beverage additives, candies, suckers, pastilles, food supplements, sprays, injectables, and suppositories.

In some embodiments, optically pure S-beta-hydroxybutyrate or a non-racemic mixture of S-beta-hydroxybutyrate and R-beta-hydroxybutyrate can be provided as a salt, such as one or more salts of alkali metals, alkaline earth metals, transition metals, amino acids, or metabolites of amino acids. Examples include lithium salts, sodium salts, potassium salts, magnesium salts, calcium salts, zinc salts, iron salts (as iron II and/or iron III), chromium salts, manganese salts, cobalt salts, copper salts, molybdenum salts, selenium salts, arginine salts, lysine salts, leucine salts, isoleucine salts, histidine salts, ornithine salts, citrulline salts, glutamine salts, and creatine salts. In some embodiments, the salt is not a calcium salt of S-beta-hydroxybutyrate.

In some embodiments, optically pure S-beta-hydroxybutyrate or a non-racemic mixture of S-beta-hydroxybutyrate and R-beta-hydroxybutyrate can be provided as one or more esters, such as mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono-ester of S-, R-, or S-R-1,3-butanediol, di-ester of S-, R-, or S-R-1,3-butanediol, mono-ester of glycerin, (3S)-hydroxybutyl (3S)-hydroxybutyrate mono-ester, (3R)-hydroxybutyl (3S)-hydroxybutyrate, mono-ester, di-ester of glycerin, tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxycarboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, and one or more polyacids, such as tartaric acid, citric acid, malic acid, succinic acid, and fumaric acid. While (3R)-hydroxybutyl (3R)-hydroxybutyrate mono-ester can be included, it should not cause the amount of R-beta-hydroxybutyrate to exceed 48% by enantiomeric equivalents.

Beta-hydroxybutyrate esters, including esters of optically pure S-beta-hydroxybutyrate and non-racemic mixtures enriched with S-beta-hydroxybutyrate relative to R-beta-hydroxybutyrate, can also be derived from alcohols such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate may include structures of beta-hydroxybutyric acid and an exemplary ester thereof (a glycerol monoester).

In some embodiments, optically pure S-beta-hydroxybutyrate can include one or more salts or esters of S-beta-hydroxybutyrate in combination with an amount of S-beta-hydroxybutyric acid. A non-racemic mixture can include one or more salts or esters of S-beta-hydroxybutyrate and R-beta-hydroxybutyrate in combination with an amount of S-beta-hydroxybutyric acid and/or R-beta-hydroxybutyric acid. The ratio of salt or ester to acid forms of S-beta-hydroxybutyrate is not necessarily the same as the ratio of salt or ester to acid forms of R-beta-hydroxybutyrate (when included). This allows for more flexibility and a broader range of advantages in controlling the pharmacokinetics and electrolyte balance of the composition.

In some embodiments, optically pure S-beta-hydroxybutyrate or a non-racemic mixture contains less than 100% of one or more beta-hydroxybutyrate salts or esters and greater than 0% free beta-hydroxybutyric acid, such as up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97%, and at least 75%, 80%, 85%, 90%, 92%, 94%, 95%, 96%, or 97%, by molar equivalents of one or more S-beta-hydroxybutyrate and/or R-beta-hydroxybutyrate salts or esters, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, and less than 25%, 20%, 15%, 10%, 8%, 6%, 5%, 4%, or 3%, by molar equivalents of free S-beta-hydroxybutyric acid and/or free R-beta-hydroxybutyric acid.

In the case where a non-racemic mixture contains a high amount of the S-enantiomer relative to the R-enantiomer, it is possible to use a higher ratio of free R-beta-hydroxybutyric acid relative to R-beta-hydroxybutyrate salt and still obtain a composition having neutral or other desired pH. That is, even if the relative amount of R-beta-hydroxybutyric acid is high relative to the R-beta-hydroxybutyrate salt, the overall amount of acid can be smaller if the amount of S-beta-hydroxybutyrate salt is higher.

In other embodiments, the non-racemic mixture can include one or more ester forms of optically pure S-beta-hydroxybutyrate, or a non-racemic mixture of S-beta-hydroxybutyrate and R-beta-hydroxybutyrate, in combination with an amount of the acid form(s) of S-beta-hydroxybutyrate and/or R-beta-hydroxybutyrate. In yet other embodiments, the non-racemic mixture can include both salt and ester forms of S-beta-hydroxybutyrate and/or R-beta-hydroxybutyrate in combination with an amount of the acid form(s) of S-beta-hydroxybutyrate and/or R-beta-hydroxybutyrate.

In some embodiments, the composition may include at least one medium chain fatty acid, or a mono-, di- or triglyceride of the at least one medium chain fatty acid, wherein the medium chain fatty acid has from 6 to 12 carbons, preferably from 8 to 10 carbons. The composition may include at least one short chain fatty acid, or a mono-, di- or triglyceride of the at least one short chain fatty acid, wherein the short chain fatty acid has less than 6 carbons. Though less preferred, the composition may include at least one long chain fatty acid, or a mono-, di- or triglyceride of the at least one long chain fatty acid, having more than 12 carbons.

Examples of short chain fatty acids include acetic acid, propionic acid, butyric acid, isobutyric acid, valeric acid, and isovaleric acid. Examples of medium chain fatty acids include caproic acid, caprylic acid, capric acid, and lauric acid. Examples of long-chain fatty acids include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids.

Examples and sources of the medium chain fatty acid, or an ester thereof such as a medium chain triglyceride, include coconut oil, coconut milk powder, fractionated coconut oil, palm oil, palm kernel oil, caprylic acid, capric acid, isolated medium chain fatty acids, such as isolated hexanoic acid, isolated octanoic acid, isolated decanoic acid, medium chain triglycerides either purified or in natural form such as coconut oil, and ester derivatives of the medium chain fatty acids ethoxylated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc.

The administration of optically pure S-beta-hydroxybutyrate or a non-racemic mixture of S-beta-hydroxybutyrate and R-beta-hydroxybutyrate results in controlled, prolonged, and modulated blood levels of ketone bodies, thereby exploiting the metabolic and physiological advantages of sustained ketosis. Raising the levels of ketone bodies in the blood provides a subject with greater flexibility in diet options as compared to methods that aim to induce and sustain ketosis based on diet alone (e.g., based on fasting and/or limited carbohydrate intake). For example, a subject that has been administered an appropriate amount of a non-racemic mixture of S-beta-hydroxybutyrate and R-beta-hydroxybutyrate will be able to cat an occasional carbohydrate or sugar-based food without jeopardizing the ketogenic state and shifting back into a glucose-based metabolic state. Further, such administration facilitates easier transitioning into a ketogenic state while reducing or eliminating the detrimental effects typically associated with entering ketosis.

In some embodiments, a ketogenic composition additionally includes a therapeutically effective amount of vitamin $D_3$. Vitamin $D_3$ is believed to work in conjunction with magnesium and calcium to promote good bone health and to prevent undesirable calcification of soft tissues. In preferred embodiments, vitamin $D_3$ is included in an amount such that an average daily dose of the ketogenic composition includes about 200 IU ("International Units") to about 8000 IU, or about 400 IU to about 4000 IU, or about 600 IU to about 3000 IU of vitamin $D_3$. In some embodiments, vitamin $D_3$ is included in an amount such that an average daily dose of the ketogenic composition includes about 5 μg to about 200 μg, or about 10 μg to about 100 μg, or about 15 μg to about 75 μg of vitamin $D_3$.

Some embodiments also include one or more additional ketone precursors or supplements. These additional ketone precursors or supplements might include acetoacetate, ketone esters, 1,3-butanediol (e.g., S-1,3-butanediol or non-racemic mixture enriched with the S-enantiomer), and/or other compounds that cause a rise in blood ketone levels without adding more electrolytes to the bloodstream. Other additives include metabolites that enhance the effect or transport of ketone bodies into mitochondria, caffeine, theobromine, and nootropics, such as L-alpha glycerylphosphorylcholine ("alpha GPC").

The composition may include flavoring agents that help mask the otherwise poor taste of beta-hydroxybutyrate compounds. These include essential oils, such as peppermint, natural and artificial sweeteners, and other flavorants known in the art.

In some embodiments, ketogenic compositions may further include one or more additional components configured to lower the hygroscopicity of the composition. For example, various anticaking agents, flow agents, and/or moisture absorbers, in types and amounts that are safe for consumption, may be included. Such additional components may include one or more of an aluminosilicate, ferrocyanide, carbonate or bicarbonate salt, silicate (e.g., sodium or calcium silicate), silica, phosphate salt (e.g., di- or tricalcium phosphate), talc, powdered cellulose, calcium carbonate, and the like.

III. COMPREHENSIVE AND AUTHORITATIVE DEFINITION OF HEART FUNCTION

As used herein, the term "heart function" is defined as a comprehensive and integrated measure of the heart's overall performance, encompassing not only its intrinsic mechanical ability to contract and relax but also its total efficacy, efficiency, and role as a regulatory and metabolic organ within the dynamic environment of the entire cardiovascular system. This definition is supported by and consistent with the established principles of cardiology and hemodynamics as defined by authoritative bodies such as the American Heart Association (AHA) and the National Heart, Lung, and Blood Institute (NHLBI).

Heart function includes, but is not limited to, the following interrelated physiological components:

Mechanical Pumping Action: The heart's primary role as a mechanical pump, which includes the rhythmic and synchronized contraction (systole) and relaxation (diastole) of its four chambers to circulate blood.

Myocardial Contractility: The intrinsic strength and force of the heart muscle's contraction, a fundamental measure of the heart's pumping power.

Cardiac Output (CO): The ultimate output of heart function, defined as the volume of blood the heart pumps per minute. It is a direct and primary indicator of overall performance and is calculated as the product of heart rate and stroke volume.

Stroke Volume (SV): The volume of blood ejected from a ventricle with each heartbeat. It is a critical measure of the heart's pumping efficiency and is directly influenced by preload, afterload, and contractility.

Ejection Fraction (EF): A vital clinical measure of systolic function, defined as the percentage of blood ejected from the ventricles with each contraction.

Preload: The volume of blood stretching the ventricular muscle fibers at the end of diastole (the filling phase). Preload is a key determinant of the force of the subsequent contraction, as described by the Frank-Starling mechanism.

Afterload (Systemic Vascular Resistance): The pressure or load against which the heart must contract to eject blood into the circulatory system. Afterload, which is directly determined by the resistance of the blood vessels (Systemic Vascular Resistance or SVR), is a critical determinant of the heart's workload and pumping efficiency.

Vascular Compliance and Elasticity: The ability of blood vessels, particularly arteries, to expand and contract in response to changes in blood pressure. This is a crucial aspect of the hemodynamic environment that directly impacts afterload and, therefore, the heart's function.

Diastolic Function: The heart's ability to relax and fill with blood. This is as important as its contractile strength for ensuring proper Cardiac Output.

Electrical Conduction: The heart's coordinated electrical rhythm, generated by its natural pacemaker (the sinoatrial node), which regulates the rate and rhythm of the heartbeat.

Metabolic Regulation: The heart's demand for and utilization of energy, including the efficient metabolism of various fuel sources like fatty acids, glucose, and ketone bodies to produce ATP.

Endocrine Signaling: The heart's role as an endocrine organ that releases hormones, such as atrial natriuretic peptide (ANP), that regulate its own function and communicate with other organs like the kidneys.

Hemodynamic Balance: The dynamic equilibrium of forces governing blood flow, pressure, and resistance throughout the circulatory system. Optimal heart function is characterized by a state of low resistance and high flow, ensuring adequate perfusion to all organs and tissues.

Blood Flow and Perfusion: A direct consequence of heart function, encompassing the rate and volume of blood circulating throughout the body, as well as the delivery of oxygen and nutrients to tissues and organs.

Therefore, any therapeutic intervention that directly or indirectly influences these above aspects is said to improve heart function. Preliminary analysis indicates that administering S-beta-hydroxybutyrate, either in optically pure form or in a non-racemic mixture enriched with S-beta-hydroxybutyrate relative to R-beta-hydroxybutyrate, can improve heart function by one or more mechanisms of action.

IV. ADMINISTRATION

In some embodiments, the compositions disclosed herein can be used in a method for increasing ketone body level, including improving metabolic function, in a subject comprising administering to a subject in need thereof a nutritionally or pharmaceutically effective amount of one or more compositions disclosed herein. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, improved body composition, or improved brain, heart, organ, or other metabolic function.

In some embodiments, administering the optically pure S-beta-hydroxybutyrate or non-racemic mixture of S-beta-hydroxybutyrate and R-beta-hydroxybutyrate in the enantiomeric ratios or percentages disclosed herein provide one or more of increased endogenous production of R-beta-hydroxybutyrate and acetoacetate; endogenous conversion of the S-beta-hydroxybutyrate into one or both of R-beta-hydroxybutyrate and acetoacetate; endogenous conversion of the S-beta-hydroxybutyrate into fatty acids and sterols; prolonged ketosis; metabolism of the S-beta-hydroxybutyrate independent of conversion to R-beta-hydroxybutyrate and/or acetoacetate; increased fetal development; increased growth years; reduced endogenous production of acetone during ketosis; signaling by the S-beta-hydroxybutyrate that modulates metabolism of R-beta-hydroxybutyrate and glucose; antioxidant activity; and production of acetyl-CoA.

Ketogenic compositions described herein may be administered to a subject in therapeutically effective dosages and/or in frequencies to induce or sustain ketosis. In some embodiments, a single dose will include an amount of S-beta-hydroxybutyrate in pure enantiomeric form, or in a non-racemic mixture enriched with S-beta-hydroxybutyrate, ranging from about 0.5 gram to about 25 grams, or about 0.75 gram to about 20 grams, or about 1 gram to about 15 grams, or about 1.5 grams to about 12 grams.

For improving metabolic function, the quantity of S-beta-hydroxybutyrate that is administered can be in a range of about 0.5 g to 30 g, such as about 2 g to about 25 g, preferably about 5 g to about 20 g, more preferably about 7.5 g to about 17.5 g, and most preferably about 10 g to about 15 g.

In some embodiments, the compositions can include or be administered together with other supplements, such as vitamin $D_3$, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

In some embodiments, the compositions may further include one or more medium chain fatty acids, fatty acid esters, or mono-, di- or triglycerides of medium chain fatty acids in order to provide an additional source of ketone bodies, as discussed herein, for sustaining ketosis for a longer period of time compared to the S-beta-hydroxybutyrate or non-racemic mixture of S-beta-hydroxybutyrate and R-beta-hydroxybutyrate by itself. In some embodiments, the composition is preferably administered such that the ratio of the S-beta-hydroxybutyrate or non-racemic mixture of S-beta-hydroxybutyrate and R-beta-hydroxybutyrate to medium chain fatty acid (or ester thereof) ranges from about 4:1 to about 1:4, or from about 2:1 to about 1:2, or from about 1.5:1 to about 1:1.5.

In some embodiments, the subject preferably follows a ketogenic diet that restricts intake of carbohydrates and protein during the period of administration of the composition. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In a preferred embodiment, ketogenic compositions can be administered via oral administration in solid and/or powdered form, such as in a powdered mixture (e.g., powder filled gelatin capsules), hard-pressed tablets, or other oral administration route known to those skilled in the art.

In some embodiments, multiple doses of the composition are administered over a period of time. The frequency of administration of the composition can vary depending on any of a variety of factors, such as timing of treatment from previous treatments, objectives of the treatment, and the like. The duration of administration of the composition (e.g., the period of time over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The compounds may be administered once, or may be divided and administered over intervals of time. It is to be understood that administration may be adjusted according to individual need and professional judgment of a person administrating or supervising the administration of the compositions.

V. EXAMPLES

The following is a description of exemplary S-beta-hydroxybutyrate and non-racemic mixtures of S-beta-hydroxybutyrate and R-beta-hydroxybutyrate compositions and other ketogenic compositions useful for raising ketone levels in a subject, including inducing and/or modulating a ketogenic state in a subject to which they are administered. It should be appreciated that the beta-hydroxybutyrate compounds described in the examples can be in the form of salts, esters, dimers, trimers, oligomers, and polymers, as discussed herein. The important thing from the standpoint of the examples is the enantiomeric percentages or ratios of S-beta-hydroxybutyrate and R-beta-hydroxybutyrate.

In some cases, the compositions can be a blend of beta-hydroxybutyrate salts, blend of beta-hydroxybutyrate esters, blend of beta-hydroxybutyrate salts and esters, blend of beta-hydroxybutyrate salts and free beta-hydroxybutyric acid(s), blend of beta-hydroxybutyrate esters and free beta-hydroxybutyric acid(s), or blend of beta-hydroxybutyrate salts, beta-hydroxybutyrate esters, and free beta-hydroxybutyric acid(s), to provide a desired electrolyte balance, taste and/or pharmacokinetic response. The compositions can also be combined with short, medium, or long chain fatty acids, esters, glycerides, and other supplements as disclosed herein to provide a desired level of elevated ketone bodies and other effects.

Example 1

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 51% by enantiomeric equivalents of the S-beta-hydroxybutyrate enantiomer and 49% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture. On the other hand, including the S-beta-hydroxybutyrate enantiomer provides for a longer state of ketosis and/or other benefits as disclosed herein.

The non-racemic mixture is readily administered as a ketogenic composition, such as in powder form as a dietary supplement mixed with food or drink, in the form of one or more capsules or tablets, or in liquid form such as a mouth spray.

Example 2

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 52% by enantiomeric equivalents of the S-beta-hydroxybutyrate enantiomer and 48% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixture of Example 1. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 3

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 53% by enantiomeric equivalents of the S-beta-hydroxybutyrate enantiomer and 47% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1 and 2. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 4

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 55% by enantiomeric equivalents of the S-beta-hydroxybutyrate enantiomer and 45% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-3. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 5

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 57% by enantiomeric equivalents of the S-beta-hydroxybutyrate enantiomer and 43% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-4. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 6

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 60% by enantiomeric equivalents of the S-beta-hydroxybutyrate enantiomer and 40% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-5. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 7

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 65% by enantiomeric equivalents of the S-beta-hydroxybutyrate enantiomer and 35% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-6. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 8

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 70% by enantiomeric equivalents of the S-beta-hydroxybutyrate enantiomer and 30% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-7. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 9

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 75% by enantiomeric equivalents of the S-beta-hydroxybutyrate enantiomer and 25% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-8. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 10

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide 80% by enantiomeric equivalents of the S-beta-hydroxybutyrate enantiomer and 20% by enantiomeric equivalents of the R-beta-hydroxybutyrate enantiomer. Because the non-racemic mixture includes less of the R-beta-hydroxybutyrate enantiomer, the onset of ketosis is delayed for a given dosage as compared to the same dosage of racemic mixture or the non-racemic mixtures of Examples 1-9. On the other hand, including the S-beta-hydroxybutyrate enantiomer provides for a longer state of ketosis and/or other benefits as disclosed herein, as compared to a composition enriched with the R-beta-hydroxybutyrate enantiomer.

Example 11

A non-racemic mixture of S-beta-hydroxybutyrate and R-beta-hydroxybutyrate is prepared by mixing one or more S-beta-hydroxybutyrate compounds with a racemic mixture of S-beta-hydroxybutyrate and R-beta-hydroxybutyrate to provide from 90%, 91%, 92%, 93%, 94%, 95%, 96%, 97%, 98%, 99%, or 99.5% by enantiomeric equivalents of the S-beta-hydroxybutyrate enantiomer and 10%, 9%, 8%, 7%, 6%, 5%, 4%, 3%, 2%, 1%, or 0.5% by enantiomeric equivalents of the R-beta-hydroxybutyrate enantiomer. Because the non-racemic mixture includes substantially less of the R-beta-hydroxybutyrate enantiomer, the onset of ketosis is significantly delayed for a given dosage as compared to the same dosage of racemic mixture or the non-racemic mixtures of Examples 1-10. On the other hand, including the S-beta-hydroxybutyrate enantiomer provides for a longer state of ketosis and/or other benefits as disclosed herein.

Example 12

A composition comprising one or more S-beta-hydroxybutyrate compounds is mixed with a carrier to form a composition with 100% equivalents of S-beta-hydroxybutyrate enantiomer and 0% equivalents of R-beta-hydroxybutyrate enantiomer. Because the composition contains no R-beta-hydroxybutyrate enantiomer, the onset of ketosis is significantly delayed for a given dosage as compared to the same dosage of racemic mixture or the non-racemic mixtures of Examples 1-11. On the other hand, including the S-beta-hydroxybutyrate enantiomer provides for a delayed and/or longer state of ketosis and/or other benefits as disclosed herein.

Example 13

Any of the foregoing examples is modified by combining optically pure S-beta-hydroxybutyrate or non-racemic mixture of S-beta-hydroxybutyrate and R-beta-hydroxybutyrate with a dietetically or pharmaceutically acceptable carrier.

Example 14

Any of the foregoing examples is modified by combining optically pure S-beta-hydroxybutyrate or non-racemic mixture of S-beta-hydroxybutyrate and R-beta-hydroxybutyrate with one or more medium chain triglycerides and/or one or more medium chain fatty acids and/or one or more mono- or diglycerides medium chain fatty acids.

Example 15

Any of the foregoing examples is modified by combining optically pure S-beta-hydroxybutyrate or non-racemic mixture of S-beta-hydroxybutyrate and R-beta-hydroxybutyrate with one or more short chain triglycerides and/or one or more short chain fatty acids and/or one or more mono- or diglycerides of short chain fatty acids Example 16

Any of the foregoing examples is modified by combining optically pure S-beta-hydroxybutyrate or non-racemic mixture of S-beta-hydroxybutyrate and R-beta-hydroxybutyrate with one or more long chain triglycerides and/or one or more long chain fatty acids and/or one or more mono- or diglycerides of long chain fatty acids Example 17

Any of the foregoing examples is modified by combining optically pure S-beta-hydroxybutyrate or non-racemic mixture of S-beta-hydroxybutyrate and R-beta-hydroxybutyrate with one or more supplements, such as vitamin $D_3$, vitamins, minerals, and others known in the art.

Example 18

Any of the foregoing examples is modified by including one or more salts of optically pure S-beta-hydroxybutyrate, or non-racemic mixture of R-beta-hydroxybutyrate and S-beta-hydroxybutyrate, and at least one of S-beta-hydroxybutyric acid or R-beta-hydroxybutyric acid to provide a mixture of S- and/or R-beta-hydroxybutyrate salt(s) and free S- and/or R-beta-hydroxybutyric acid(s), where the mixture contains less than 100% of the one or more beta-hydroxybutyrate salts and greater than 0% of the free beta-hydroxybutyric acid(s), including up to 99.9%, 99.8%, 99.7%, 99.6%, 99.5%, 99.4%, 99.3%, 99.2%, 99.1%, 99%, 98.8%, 98.65%, 98.5%, 98.35%, 98.2%, 98%, 97.75%, 97.5%, 97.25%, or 97% by molar equivalents of one or more S-beta-hydroxybutyrate and/or R-beta-hydroxybutyrate salts, and at least 0.1%, 0.2%, 0.3%, 0.4%, 0.5%, 0.6%, 0.7%, 0.8%, 0.9%, 1%, 1.2%, 1.35%, 1.5%, 1.65%, 1.8%, 2%, 2.25%, 2.5%, 2.75%, or 3%, by molar equivalents of free S-beta-hydroxybutyric acid and/or free R-beta-hydroxybutyric acid.

Example 19

Any of the foregoing examples is modified by including one or more esters of S-beta-hydroxybutyrate and/or R-beta-hydroxybutyrate and at least one of S-beta-hydroxybutyric acid or R-beta-hydroxybutyric acid to provide a mixture of beta-hydroxybutyrate ester(s) and free S- and/or R-beta-hydroxybutyric acid(s), where the mixture contains less than 100% of the one or more beta-hydroxybutyrate esters and greater than 0% free beta-hydroxybutyric acid.

Example 20

Any of the foregoing compositions is administered so as to provide from 10-15 g of S-beta-hydroxybutyrate compounds, either in enantiomerically pure form or in a non-racemic mixture that contains a minor amount of R-beta-hydroxybutyrate compounds. The compositions improve brain, heart, organ, and other metabolic functions in subjects, including providing energy to the heart, dilating the arteries, decreasing blood pressure and systemic vascular resistance, and increasing cardiac output In some embodiments, the amount of S-beta-hydroxybutyrate administered to the subject is effective to improve brain, heart, and organic function by providing energy that can be readily utilized by the brain, heart, organs, and peripheral tissues, but does not affect insulin or triglyceride levels in a subject. Increasing the amount of S-beta-hydroxybutyrate administered to the subject generally increases the beneficial effects on the brain, heart, organs, and other metabolic functions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for improving metabolic function in a subject, comprising:

one or more esters of optically pure S-beta-hydroxybutyrate or one or more esters of a non-racemic mixture of S-beta-hydroxybutyrate and R-beta-hydroxybutyrate containing more than 50% and less than 100% by enantiomeric equivalents of at least one S-beta-hydroxybutyrate ester and less than 50% and more than 0% by enantiomeric equivalents of at least one R-beta-hydroxybutyrate ester.

2. The composition of claim 1, wherein the composition comprises one or more esters of S-beta-hydroxybutyrate and at least one component selected from the group consisting of ethanol, 1-propanol, 1,2-propanediol, 1,3-propanediol, 1,3-butanediol, glycerin, S-beta-hydroxybutyrate R-beta-hydroxybutyrate, acetoacetate, dimers, trimers, oligomers, or polyesters containing repeating units of beta-hydroxybutyrate, and complex oligomers or polymers of beta-hydroxybutyrate and one or more carboxylic acids selected from lactic acid, citric acid, quinic acid, shikimic acid, salicylic acid, tartaric acid, malic acid, succinic acid, and fumaric acid.

3. The composition of claim 1, wherein the composition comprises one or more esters of S-beta-hydroxybutyrate and at least one component selected from the group consisting of altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, and threitol.

4. The composition of claim 1, wherein the composition comprises a mixture of S-beta-hydroxybutyrate ester and at least one of S-beta-hydroxybutyric acid or S-beta-hydroxybutyrate salt.

5. The composition of claim 1, wherein the composition comprises a non-racemic mixture that contains 50.5% to 99.5% by enantiomeric equivalents of S-beta-hydroxybutyrate ester and 49.5% to 0.5% by enantiomeric equivalents of R-beta-hydroxybutyrate ester, or 51% to 99% by enantiomeric equivalents of S-beta-hydroxybutyrate ester and 49% to 1% by enantiomeric equivalents of R-beta-hydroxybutyrate ester, or 52% to 98% by enantiomeric equivalents of S-beta-hydroxybutyrate ester and 48% to 2% by enantiomeric equivalents of R-beta-hydroxybutyrate ester.

6. The composition of claim 1, further comprising an ester of optically pure S-1,3-butanediol or an ester of a non-racemic mixture enriched with S-1,3-butanediol relative to R-1,3-butanediol.

7. The composition of claim 1, wherein the composition further comprises at least one medium chain fatty acid having 6 to 12 carbons or ester thereof.

8. The composition of claim 1, wherein the composition further comprises at least one short chain fatty acid having less than 6 carbons, or a mono-, di- or triglyceride of the at least one short chain fatty acid.

9. The composition of claim 1, wherein the composition improves brain function in the subject.

10. The composition of claim 1, wherein the composition improves heart function in the subject.

11. The composition of claim 1, wherein the composition improves organ function in the subject.

12. A kit for administering the composition of claim 1 to a subject, comprising:

a container in which the composition is placed, wherein the container is selected from the group consisting of carton, box, can, jar, bag, pouch, bottle, jug, liquid squeeze bottle with integrated measuring device, and keg; and a measuring device configured to hold therein a unit dose, or fraction thereof, of the composition, wherein the measuring device is selected from the group consisting of cup, scoop, syringe, dropper, spatula, spoon, and colonic irrigation device.

13. A composition for improving metabolic function in a subject, comprising:

one or more esters of optically pure S-beta-hydroxybutyrate or one or more esters of a non-racemic mixture of S-beta-hydroxybutyrate and R-beta-hydroxybutyrate containing more than 50% and less than 100% by enantiomeric equivalents of at least one S-beta-hydroxybutyrate ester and less than 50% and more than 0% by enantiomeric equivalents of at least one R-beta-hydroxybutyrate ester, wherein the composition is provided as or in a tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, or suppository.

14. The composition of claim 13, wherein the composition comprises one or more esters of S-beta-hydroxybutyrate and at least one component selected from the group consisting of ethanol, 1-propanol, 1,2-propanediol, 1,3-propanediol, 1,3-butanediol, glycerin, S-beta-hydroxybutyrate R-beta-hydroxybutyrate, acetoacetate, dimers, trimers, oligomers, or polyesters containing repeating units of beta-hydroxybutyrate, and complex oligomers or polymers of beta-hydroxybutyrate and one or more carboxylic acids selected from lactic acid, citric acid, quinic acid, shikimic acid, salicylic acid, tartaric acid, malic acid, succinic acid, and fumaric acid.

15. The composition of claim 13, wherein the composition comprises one or more esters of S-beta-hydroxybutyrate and at least one component selected from the group consisting of altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, and threitol.

16. The composition of claim 13, wherein the composition improves metabolic function of at least one of the subject's brain, heart, or other organ.

17. A composition for improving metabolic function in a subject, comprising:

a dietetically or pharmaceutically acceptable carrier selected from the group consisting of tablet, capsule, powder, food product, food additive, flavored beverage, vitamin fortified beverage, non-alcoholic beverage, flavored beverage additive, vitamin fortified beverage additive, non-alcoholic beverage additive, candy, sucker, pastille, food supplement, flavored mouth spray, and suppository; and one or more esters of optically pure S-beta-hydroxybutyrate or one or more esters of a non-racemic mixture of S-beta-hydroxybutyrate and R-beta-hydroxybutyrate containing more than 50% and less than 100% by enantiomeric equivalents of at least one S-beta-hydroxybutyrate ester and less than 50% and more than 0% by enantiomeric equivalents of at least one R-beta-hydroxybutyrate ester.

18. The composition of claim 17, wherein the composition comprises one or more esters of S-beta-hydroxybutyrate and at least one component selected from the group consisting of ethanol, 1-propanol, 1,2-propanediol, 1,3-propanediol, 1,3-butanediol, glycerin, S-beta-hydroxybutyrate R-beta-hydroxybutyrate, acetoacetate, dimers, trimers, oligomers, or polyesters containing repeating units of beta-hydroxybutyrate, and complex oligomers or polymers of beta-hydroxybutyrate and one or more carboxylic acids selected from lactic acid, citric acid, quinic acid, shikimic acid, salicylic acid, tartaric acid, malic acid, succinic acid, and fumaric acid.

19. The composition of claim 17, wherein the composition comprises one or more esters of S-beta-hydroxybutyrate and at least one component selected from the group consisting of altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, and threitol.

20. The composition of claim 17, wherein the composition improves metabolic function of at least one of the subject's brain, heart, or other organ.

* * * * *